United States Patent [19]

Stephan

[11] 4,087,437
[45] May 2, 1978

[54] 2-PHENYL-5-BENZOXAZOLYLALKANOIC ACID PURIFICATION PROCESS

[75] Inventor: Erwin A. Stephan, Indianapolis, Ind.

[73] Assignee: Eli Lilly and Company, Indianapolis, Ind.

[21] Appl. No.: 720,710

[22] Filed: Sep. 7, 1976

[51] Int. Cl.² ............................................. C07D 263/56
[52] U.S. Cl. ................................................ 260/307 D
[58] Field of Search .................................... 260/307 D

[56] References Cited

U.S. PATENT DOCUMENTS

| 3,849,489 | 11/1974 | Rudzki | 260/525 |
| 3,912,748 | 10/1975 | Evans et al. | 260/307 D |

Primary Examiner—Raymond V. Rush
Attorney, Agent, or Firm—James L. Rowe; Everet F. Smith

[57] ABSTRACT

Crude preparations of 2-phenyl-5-benzoxazolylalkanoic acids are purified by forming the ammonium salt thereof in an organic solvent and thermally reconverting the separated ammonium salt to the acid. Gaseous ammonia is a by-product.

8 Claims, No Drawings

2-PHENYL-5-BENZOXAZOLYLALKANOIC ACID PURIFICATION PROCESS

BACKGROUND OF THE INVENTION

2-Phenyl or 2-(substituted phenyl)-5-(or 6)-benzoxazolylalkanoic acids, highly useful anti-inflammatory agents, are disclosed and claimed in U.S. Pat. No. 3,912,748. One of the most active of these acids, dl-α-(2-[4-chlorophenyl]-5-benzoxazolyl)propionic acid, also named dl-2-(4-chlorophenyl)-α-methyl-5-benzoxazolylacetic acid, has been given the generic name "benoxaprofen" and is currently undergoing a clinical trial as a non-steroidal anti-inflammatory agent of particular value in the treatment of rheumatoid arthritis and related diseases. The chemistry and pharmacology of these 2-aryl-5-benzoxazolyl alkanoic acids is to be found in *J. Med. Chem.*, 18, 53 (1975). In general, benzoxazolyl alkanoic acids are prepared by hydrolysis of the corresponding nitrile followed by a purification step involving recrystallization from an organic solvent. Benoxaprofen prepared by such a procedure has been found to crystallize from organic solvents in two different forms, known as Form I and Form II. Crystalline Form II is considerably more stable than Form I on being aged at relatively high temperature, and this increased stability carries over into pharmaceutical formulations containing the compound.

It has been known to purify benzoic and terephthalic acids obtained by the hydrolysis of their respective nitriles by formation of the ammonium salt, separation of the thus formed ammonium salt from impurities followed by decomposition by heat of the ammonium salt to yield the free acid and gaseous ammonia as a volatile byproduct. (See for example, U.S. Pat. No. 3,876,691 or U.S. Pat. No. 3,849,489).

It is an object of this invention to provide a method for purifying dl-2-(4-chlorophenyl)acid-α-methyl-5-benzoxazolylacetic acid and related compounds which yields the desired compound in a high degree of purity employing a relatively simple chemical process which does not require expensive equipment, and furnishes benoxaprofen in the desirable crystalline Form II when used to purify this compound.

SUMMARY OF THE INVENTION

In fulfillment of the above and other objects, this invention provides a process whereby a compound of structure I

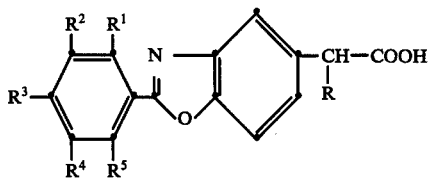

wherein R is H or $CH_3$, wherein each of $R^1$, $R^2$, $R^3$, $R^4$, and $R^5$, when taken singly, are members of the group consisting of halogen, nitro, methyl, and methoxy, or when taken in adjacent pairs, form a methylenedioxy radical, subject to the proviso that at least three of $R^1$, $R^2$, $R^3$, $R^4$ and $R^5$ are hydrogen in a given molecule, is treated with ammonium hydroxide or gaseous ammonia to form an ammonium salt, isolating said ammonium salt, and heating the thus isolated ammonium salt to a temperature in the range of 90°–160° C. thereby decomposing said ammonium salt and providing the compound of structure I in purified form.

In carrying out my novel procedure, a 2-phenyl (or substituted phenyl)-5-benzoxazolyl alkanoic acid prepared by the procedure of Example 1 of U.S. Pat. No. 3,912,748 or of other examples of that patent such as Examples 20, 24, 25 and 27, is dissolved without further purification, in an inert polar solvent or mixture of solvents and the resulting solution is filtered. Concentrated aqueous ammonium hydroxide or gaseous ammonia is added slowly to the filtrate. During this addition, the ammonium salt of the 2-phenyl (or substituted phenyl)-5-benzoxazolyl alkanoic acid precipitates to yield a slurry. The slurry is chilled and the pH checked, either with use of pH paper or by diluting an aliquot of the slurry with water and measuring the pH of the supernatant liquid, using either a pH meter or pH paper. If the pH is below about 9, sufficient concentrated aqueous ammonium hydroxide is added to bring the pH up to that level. The precipitated ammonium salt is then separated by filtration and the filter cake washed with cold acetone or other suitable solvent. The filter cake is then dried at a temperature above 90° C., but below 160° C., preferably at a temperature in the range 100°–150° C. During the drying process at this temperature, the ammonium salt is decomposed to yield again the now purified 2-phenyl (or substituted phenyl)-5-benzoxazolyl alkanoic acid. Drying is continued until the decomposition of the ammonium salt is substantially complete. The yield of purified material is usually in the range 95–98 percent.

Alternatively, the ammonium salt can be suspended in a solvent boiling in the range 90°–160° C. and the resulting suspension or slurry heated, preferably at reflux; i.e., at the boiling point of the solvent, until the ammonium salt is substantially completely decomposed to ammonia and the free purified alkanoic acid. If the purified alkanoic acid thus produced is substantially insoluble in the solvent used to slurry the ammonium salt (n-octane for example), the same crystalline form will be obtained as from heating the salt in the absence of a solvent. For example, dl-2-(4-chlorophenyl)-α-methyl-5-benzoxazolylacetic acid will be obtained in crystalline Form II by heating in n-octane. If the benzoxazolyl alkanoic acid is soluble in the solvent used to slurry the ammonium salt, (n-butyl acetate for example), a recrystallized product will be obtained. With either type of solvent the alkanoic acid is separated from the solvent as by decantation or filtration. If the alkanoic acid is soluble, the solution is ordinarily concentrated and/or chilled to increase crystallization and further crystals are obtained from the mother liquor.

An additional advantage of my novel process is the fact that, with certain solvents such as n-butyl acetate, a more stable crystalline form such as Form II of dl-2-(4-chlorophenyl)-α-methyl-5-benzoxcazolylacetic acid can be obtained in a denser condition than that obtained directly by decomposition of the ammonium salt. Denser, more closely packed crystals have obvious advantages in formulating a compound for clinical use in tablets, capsules and other solid pharmaceutical forms.

Among the inert polar solvents used to dissolve the 2-phenyl-(or substituted phenyl)-5-benzoxazolyl alkanoic acid prior to ammonium salt formation are included dimethylformamide (DMF), dimethylsulfoxide (DMSO), acetone, chloroform, ethylene dichloride, or combinations of these. Ammonium hydroxide or gaseous ammonia is slowly added to the solution of the benzoxazolyl alkanoic acid in one of these solvents. Usually concentrated aqueous ammonium hydroxide (14N or 28 percent) is employed in salt formation although use of anhydrous ammonia permits maintenance of anhydrous reaction conditions. The addition with either source of ammonia takes place slowly so as to encourage the formation of pure, filterable, crystals. After all of the benzoxazolyl alkanoic acid in solution has all been converted to the corresponding ammonium salt, the pH of the resulting solution should be about 9. If the pH is less than 9, additional concentrated ammonium hydroxide is added.

The reconversion of the ammonium salt to the free acid takes place by heating at a temperature in the range 90°–160° C. As previously stated, the heating can be accomplished by use of a dryer above 90° C or by slurrying the ammonium salt in a solvent boiling above about 90° C. and heating the resulting suspension to a temperature in the range 90°–160° C. which may be the boiling point of the solvent. Any conventional dryer can be used including tray dryers, fluidized bed dryers, double cone dryers, forced air dryers, and the like. Likewise, any solvent boiling above 90° C. can be employed although preferably, the solvent should either be one in which the benzoxazolyl alkanoic acid product is either insoluble, or, if soluble, will yield the most desirable crystalline form of the benzoxazolyl alkanoic acid product. With mechanical dryers, the heating time required; i.e., time to substantially completely convert the ammonium salt to the free acid, will naturally vary according to (a) the temperature employed (b) which dryer is used, (c) the efficiency of the dryer, and (d) the degree of purity desired in the final product. Times of from 10 minutes to 15 hours have been used. Preferably, the free acid is dried (heated) till only minimal quantities of ammonia are detectable and then to constant weight if a certain degree of purity, in the sense of freedom from volatile impurities, is desired. Prolonged heating at the upper end of the heating range should be avoided because of the increased possibility of decomposition of the free acid.

Illustrative heating times are as follows: at a temperature of about 95° C. in a tray dryer, for example, a minimum time of 6 hours is necessary to convert the ammonium salt to the free acid in better than 95 percent yield, whereas at 155° C., ½ hour heating for the same degree of conversion is sufficient. Recoveries of 98 percent of starting acid and purities of 99 percent or better of purified acid are common utilizing my novel process.

Some of the acids which can be purified by the above procedure include the following:

dl-2-(2-p-Fluorophenyl)-α-methyl-5-benzoxazolylacetic acid,
dl-2-(2-p-Chlorophenyl)-α-methyl-5-benzoxazolylacetic acid,
dl-2-(2-m-Chlorophenyl)-α-methyl-5-benzoxazolylacetic acid,
dl-2-(2-p-Methylphenyl)-α-methyl-5-benzoxazolylacetic acid,
dl-2-(2-m-Methylphenyl)-α-methyl-5-benzoxazolylacetic acid,
dl-2-(2-o-Methylphenyl)-α-methyl-5-benzoxazolylacetic acid,
dl-2-(2-p-Methoxyphenyl)-α-methyl-5-benzoxazolylacetic acid,
dl-2-(2-o-Hydroxy-p-chlorophenyl)-α-methyl-5-benzoxazolylacetic acid,
dl-2-(2-phenyl)-α-methyl-5-benzoxazolylacetic acid,
dl-2-[2-(3,4-Methylenedioxyphenyl)]-α-methyl-5-benzoxazolylacetic acid,
dl-2-[2-(3,4-Dichlorophenyl)]-α-methyl-5-benzoxazolylacetic acid,
dl-2-[2-(2,4-Dichlorophenyl)]-α-methyl-5-benzoxazolylacetic acid,
dl-2-(2-o-Chlorophenyl)-α-methyl-5-benzoxazolylacetic acid,
dl-2-(2-p-Iodophenyl)-α-methyl-5-benzoxazolylacetic acid,
dl-2-(2-m-Fluorophenyl)-α-methyl-5-benzoxazolylacetic acid,
dl-2-[2-(3,5-Dichlorophenyl)]-α-methyl-5-benzoxazolylacetic acid,
dl-2-(2-o-Fluorophenyl)-5-benzoxazolylacetic acid,
dl-2-(p-chlorophenyl)-5-benzoxazolylacetic acid,
dl-2-phenyl-5-benzoxazolylacetic acid.

This invention is further illustrated by the following specific examples:

EXAMPLE 1

41 kg. of dl-2-(p-chlorophenyl)-α-methyl-5-benzoxazolylacetonitrile were hydrolyzed in 12N aqueous hydrochloric acid by being stirred at 80° C. for about 2 hours. The reaction mixture was cooled to about 40° C. and then poured slowly with vigorous stirring into cold water. The solid precipitate of dl-2-(p-chlorophenyl)-α-methyl-5-benzoxazolylacetic acid thus prepared was collected by filtration and the filter cake washed with water until the washings no longer gave an acidic reaction to litmus. The filter cake was dried at 70°–80° C.; yield = 40 kg. (77 percent purity). The filter cake was dissolved in 48.3 liters of DMF at 55° C. and the resulting solution diluted with about 180 liters of acetone. The resulting solution was filtered. The filtrate was collected and about 11 liters of 28 percent aqueous ammonium hydroxide were added very slowly to the filtrate maintained at about 35° C over a period of about ½ hour. During the addition of the aqueous ammonium hydroxide, the ammonium salt of dl-2-(p-chlorophenyl)-α-methyl-5-benzoxazolylacetic acid slowly precipitated yielding a slurry. After the addition of the ammonium hydroxide had been completed, the pH of the slurry was checked and found to be about 9. The slurry was next chilled in an ice-water mixture to about 0° C. and the precipitated ammonium salt separated by filtration. The filter cake was washed with cold acetone (0° C.) The washed filter cake was dried at 125° C. for 3 hours in a tray dryer. During this heating and drying period, the ammonium salt decomposed yielding the free acid, dl-2-(p-chlorophenyl)-α-methyl-5-benzoxazolylacetic acid in the desired Form II crystals. 29.65 kg. of purified free acid were obtained assaying about 95 percent purity by NMR. Using the same drying system, the following times and temperatures were found to give 97 percent or better purity free acid: 6 hours at 95° C., 2.5 hours at 125° C., 1.5 hours at 140° C., 0.5 hours at 155° C.

It is a particular advantage of this process that dl-2-(p-chlorophenyl)-α-methyl-5-benzoxazolylacetic acid purified by the above process crystallizes in Form II crystals. Form II crystals of the above compound are considerably more stable than Form I crystals and are the preferred crystalline form for use in pharmaceutical formulations for administration as an anti-inflammatory agent. Form II crystals of dl-2-(p-chlorophenyl)-α-methyl-5-benzoxazolylacetic acid have the following X-ray powder diffraction pattern using filtered copper-nickel radiation at λ=1.5405.

| "d" in A. | I/I° |
|---|---|
| 11.77 | 10 |
| 8.06 | 10 |
| 7.07 | 70 |
| 5.67 | 100 |
| 5.30 | 10 |
| 5.06 | 20 |
| 4.79 | 10 |
| 4.41 | 50 |
| 4.17 | 80 |
| 3.93 | 05 |
| 3.65 | 30 |
| 3.56 | 90 |
| 3.24 | 60 |
| 3.09 | 40 |
| 3.03 | 15 |
| 2.97 | 15 |
| 2.81 | 05 |
| 2.75 | 05 |
| 2.66 | 05 |
| 2.57 | 05 |
| 2.37 | 10 |
| 2.29 | 05 |
| 2.15 | 05 |
| 2.04 | 15 |
| 1.98 | 20 |
| 1.91 | 05 |
| 1.78 | 02 |

Other solvent combinations can be used in the above salt formation step including mixtures of DMSO or DMF with chloroform, ethylene dichloride or acetone.

With other dryers such as a fluidized bed dryer, shorter ammonium salt decomposition time are required. For example, the following ammonia percentages were detected after certain time intervals, using about a 110° C. dryer temperature and dl-2-(4-chlorophenyl)-α-methyl-5-benzoxazolyl acetic acid ammonium salt.

| Time | Percent NH₃ |
|---|---|
| 0.5 hrs. | .40 |
| 1.0 hrs. | .26 |
| 1.5 hrs. | .22 |
| 2.0 hrs. | .12 |
| 2.5 hrs. | .10 |

EXAMPLE 2

Twenty-five and three tenths kilograms of dl-2-(4-chlorophenyl)-α-methyl-5-benzoxazolylacetic acid ammonium salt (dry-basis), prepared as in Example 1, were slurried with 430 l. of n-butyl acetate. The slurry was heated at 125° C. to drive off residual chloroform. The slurry was then heated for 3 hours at a temperature in the range 120°-125° C. (reflux temperature) under a nitrogen purge. The resulting mixture containing dl-2-(4-chlorophenyl)-α-methyl-5-benzoxazolylacetic acid formed by decomposition of the above ammonium salt was cooled to 90° C.; 15 kg. of activated carbon and 5 kg. of a cellulosic filter-acid were added. The resulting mixture was stirred for 30 minutes and then filtered. The filter cake was then washed three times with 20 l. portions of n-butyl acetate. The filtrate was concentrated by removing 330-340 l. of n-butyl acetate by distillation. The concentrated filtrate was cooled to about −5° C. dl-2-(4-Chlorophenyl)-α-methyl-5-benzoxazolylacetic acid precipitated and was separated by filtration. The filter cake was washed three times with 151 portions of cold (0° C.) methanol, and was then dried at 80° C. for 12 hours in a forced hot air dryer. Yield = 21.5 kg.; assay 98.2 percent of Form II crystals. Other runs yielded 22.6 kg. with assays as high as 99.5 percent. 5-7 Percent additional acid can be recovered from the filtrate plus washings. The solvent remaining is customarily recycled.

n-Octane can be substituted for n-butyl acetate in the above procedure with similar results. The procedure is modified however by omitting the charcoal decolorizing step since the acid is insoluble in n-octane and is obtained directly by filtration of the heated slurry after cooling.

The following are typical yields and product assays for different variations on the procedures of Examples 1 and 2. In each instance, the ammonium salt was prepared in DMF-chloroform with concentrated aqueous ammonia.

| Procedure | Overall Yield | Assay |
|---|---|---|
| Heat solid acid in air dryer | 95–96 percent | 97.4–98.8 percent |
| n-butyl acetate | 85 percent | 98.2 percent |
| n-butyl acetate with carbon treatment | 85 percent | 99.5 percent |
| n-octane | 91 percent | 97.5 percent |

I claim:
1. A process which comprises reacting dl-2-(4-chlorophenyl)-2-methyl-5-benzoxazolylacetic acid isolated from the acidic hydrolysis of the corresponding nitrile without further purification;
   with ammonium hydroxide in an inert solvent to form an ammonium salt;
   isolating said ammonium salt, and
   then heating the thus-isolated ammonium salt to a temperature in the range of 90°-160° C. thereby decomposing said ammonium salt and providing said dl-2-(4-chlorophenyl)-2-methyl-5-benzoxazolylacetic acid as Form II crystals.

2. A process according to claim 1 in which the ammonium salt is decomposed by heating in a solvent in which dl-2-(4-chlorophenyl)-2-methyl-5-benzoxazolylacetic acid is insoluble.

3. A process according to claim 2 in which dl-2-(4-chlorophenyl-2-methyl-5-benzoxazolylacetic acid is separated from the solvent.

4. A process according to claim 1 in which the ammonium salt of dl-2-(4-chlorophenyl)-α-methyl-5-benzoxazolylacetic acid is decomposed by heating in n-octane.

5. A process according to claim 1 in which the ammonium salt is decomposed by heating in solvent in which the resulting dl-2-(4-chlorophenyl)-2-methyl-5-benzoxazolylacetic acid is soluble.

6. A process according to claim 5 in which the ammonium salt of dl-2-(4-chlorophenyl)-α-methyl-5-benzoxazolylacetic acid is decomposed by heating in n-butyl acetate.

7. A process according to claim 6 in which the dl-2-(4-chlorophenyl)-2-methyl-5-benzoxazolylacetic acid is obtained in crystalline Form II by chilling the n-butyl acetate solution and separating the precipitated dl-2-(4-chlorophenyl)-2-methyl-5-benzoxazolylacetic acid therefrom.

8. A process according to claim 5, in which dl-2-(4-chlorophenyl-2-methyl-5-benzoxazolylacetic acid is separated from the solvent.

* * * * *